(12) United States Patent
Gifford et al.

(10) Patent No.: US 10,403,393 B2
(45) Date of Patent: Sep. 3, 2019

(54) VOICE-ASSISTED CLINICAL NOTE CREATION ON A MOBILE DEVICE

(71) Applicant: CERNER INNOVATION, INC., Kansas City, KS (US)

(72) Inventors: Thomas C. Gifford, Kansas City, MO (US); Bryan T. Rose, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 410 days.

(21) Appl. No.: 14/314,323

(22) Filed: Jun. 25, 2014

(65) Prior Publication Data

US 2015/0379200 A1 Dec. 31, 2015

(51) Int. Cl.
*G16H 10/60* (2018.01)
*G06F 19/00* (2018.01)
*G10L 15/00* (2013.01)

(52) U.S. Cl.
CPC ............ *G16H 10/60* (2018.01); *G06F 19/00* (2013.01); *G10L 15/00* (2013.01); *Y02A 90/26* (2018.01)

(58) Field of Classification Search
CPC .......... G06F 19/322–327; G10L 15/00; G16H 10/60; Y02A 90/26
See application file for complete search history.

(56) References Cited

U.S. PATENT DOCUMENTS

| | | | |
|---|---|---|---|
| 8,195,468 B2 | 6/2012 | Weider et al. | |
| 8,612,230 B2 | 12/2013 | Agapi et al. | |
| 2002/0082868 A1* | 6/2002 | Pories | G06F 19/322 705/3 |
| 2012/0101847 A1 | 4/2012 | Johnson et al. | |
| 2012/0215557 A1 | 8/2012 | Flanagan et al. | |
| 2012/0253801 A1 | 10/2012 | Santos-Iang et al. | |
| 2014/0012790 A1* | 1/2014 | Oberkampf | G16H 50/20 706/46 |
| 2014/0222462 A1* | 8/2014 | Shakil | G06Q 50/22 705/3 |
| 2015/0294089 A1* | 10/2015 | Nichols | G06F 19/327 705/3 |

* cited by examiner

*Primary Examiner* — Sheetal R Paulson
(74) *Attorney, Agent, or Firm* — Shook, Hardy and Bacon LLP

(57) ABSTRACT

Methods, systems, and computer-readable media are provided for facilitating the voice-assisted creation of a shorthand clinical note on a mobile or tablet device. A microphone on the device is used to capture a conversation between a clinician and a patient. Clinically-relevant concepts in the conversation are identified, extracted, and temporarily presented on the device's touch screen interface. The concepts are selectable, and upon selection, the selected concept is populated into a clinical note display area of the touch screen interface. The shorthand clinical note may be used as a memory prompt for the later creation of a more comprehensive clinical note.

18 Claims, 11 Drawing Sheets

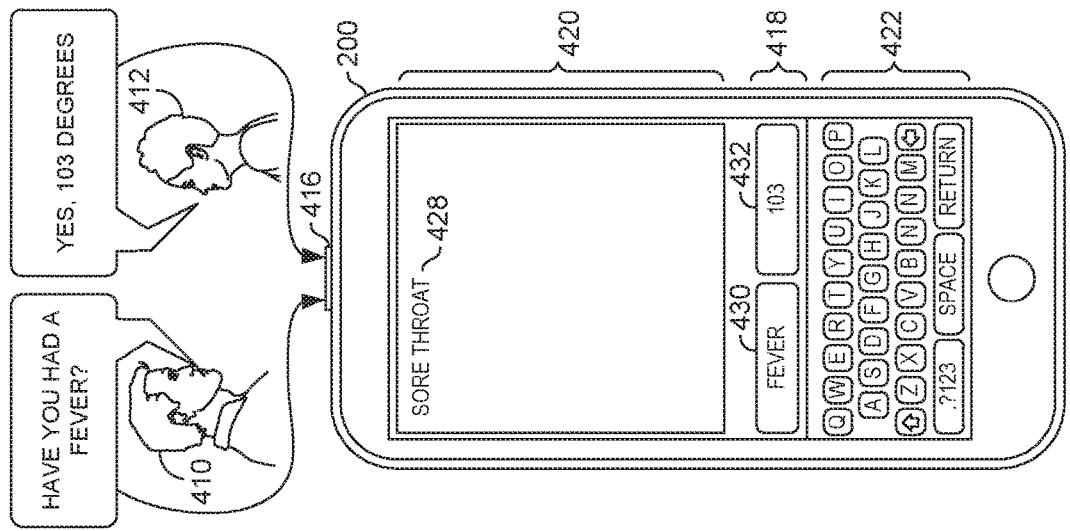
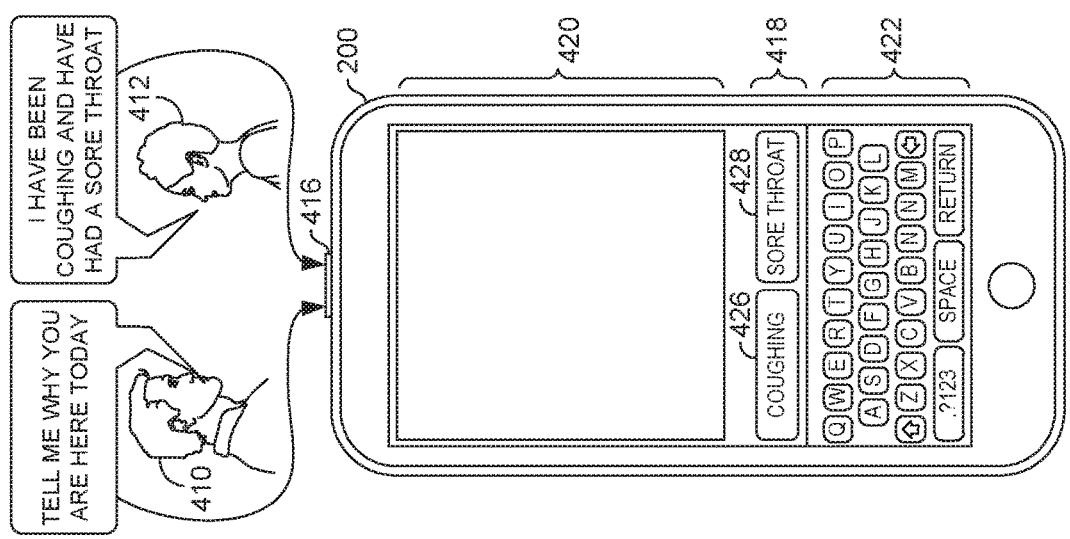
FIG. 4A.
FIG. 4B.

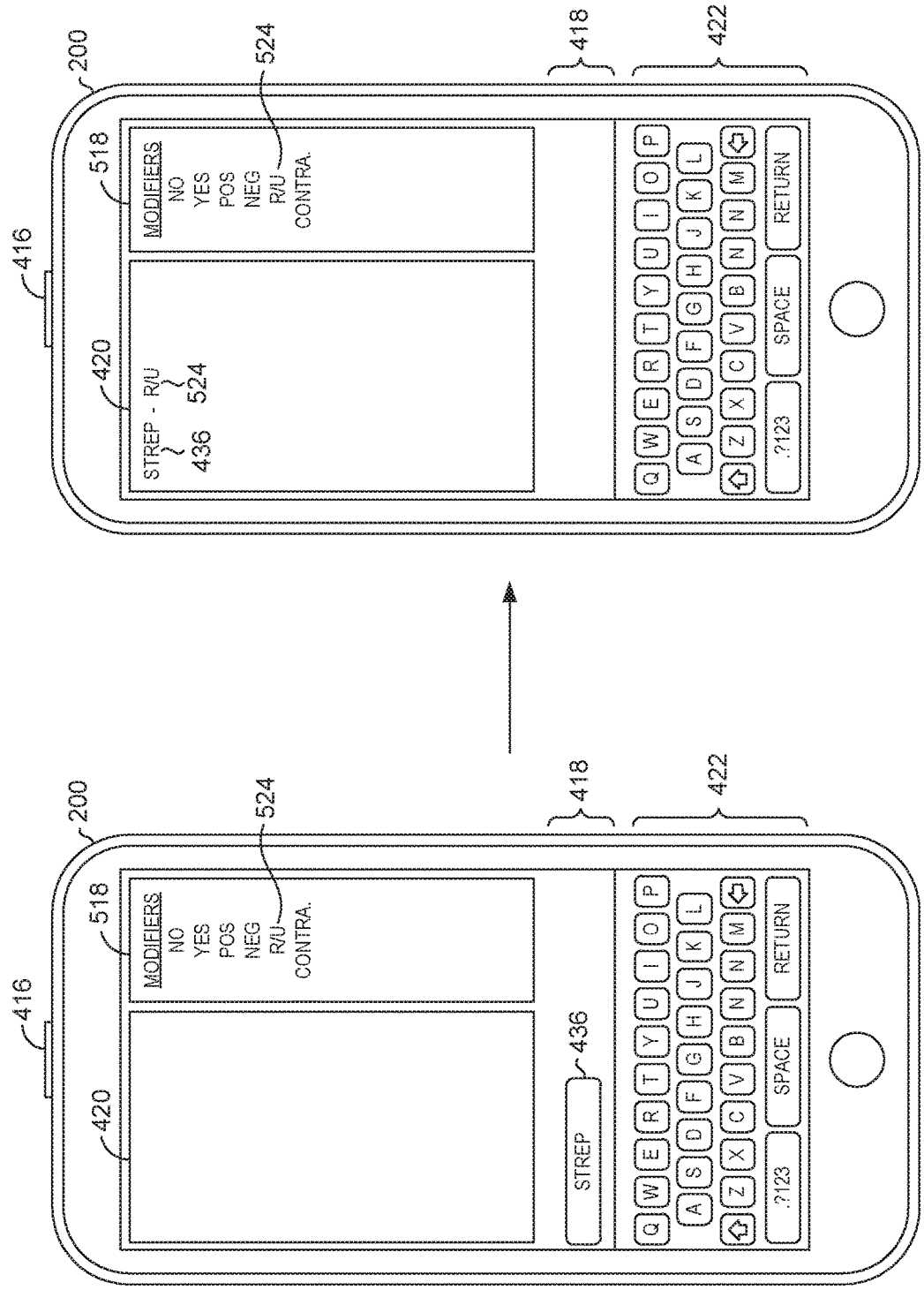

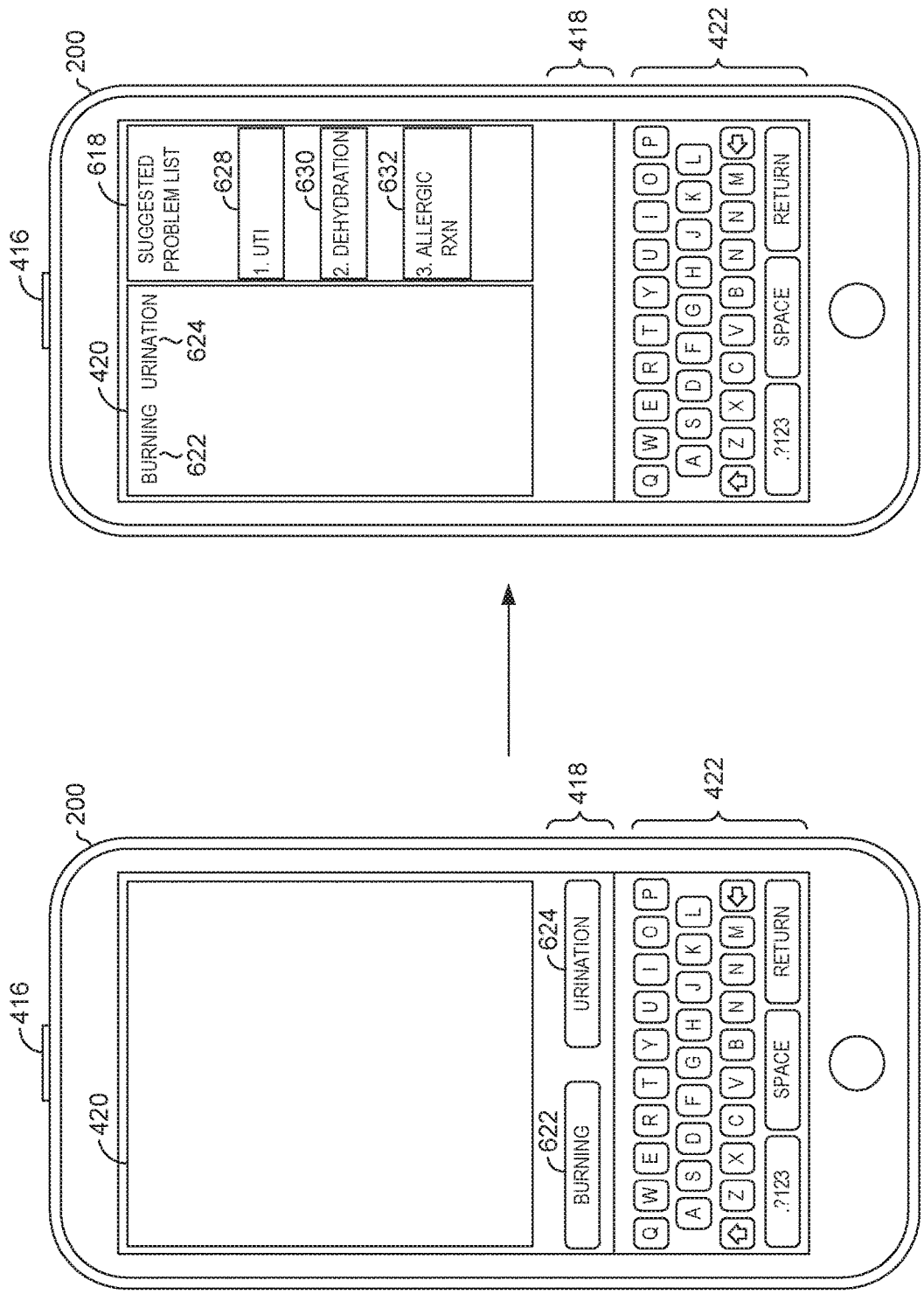

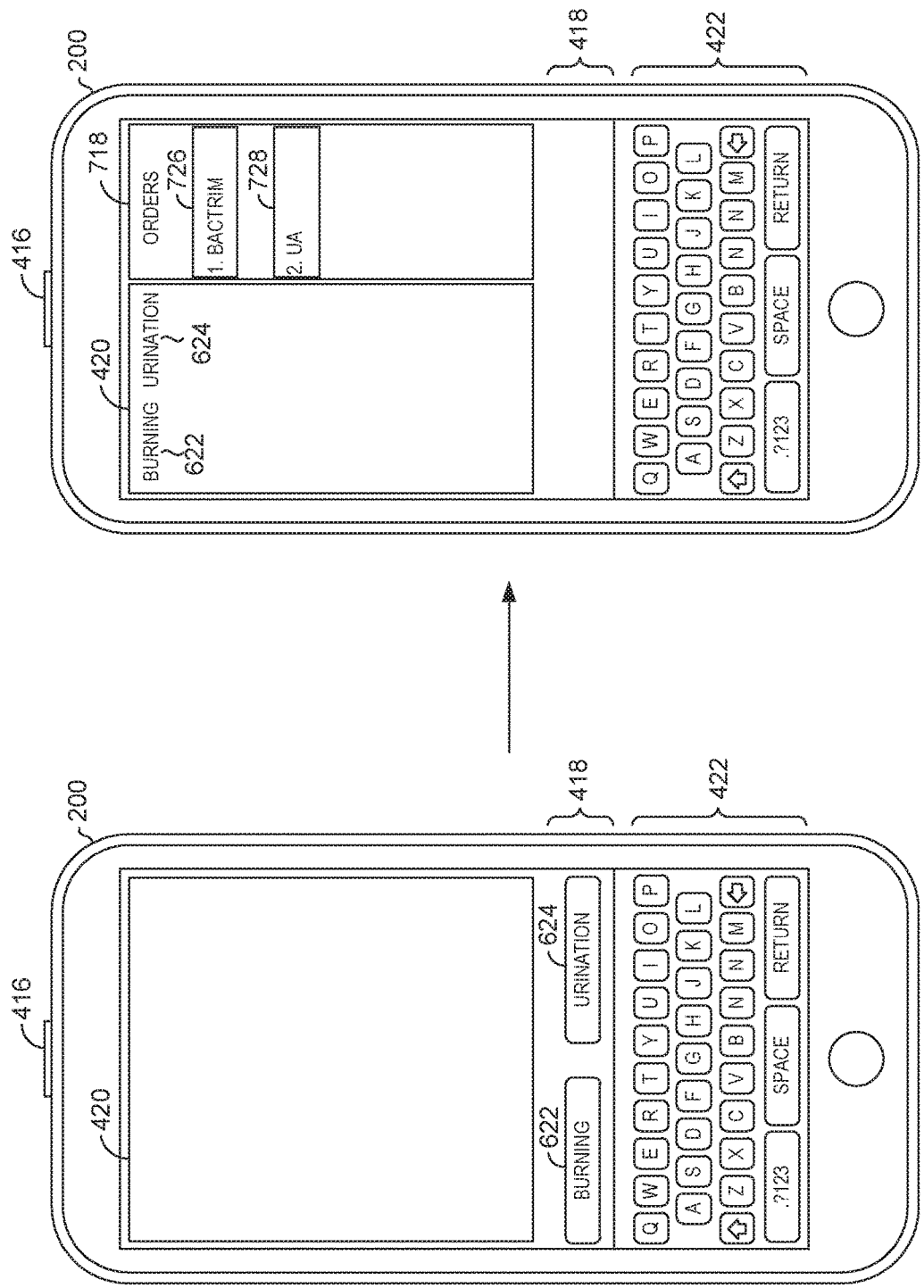

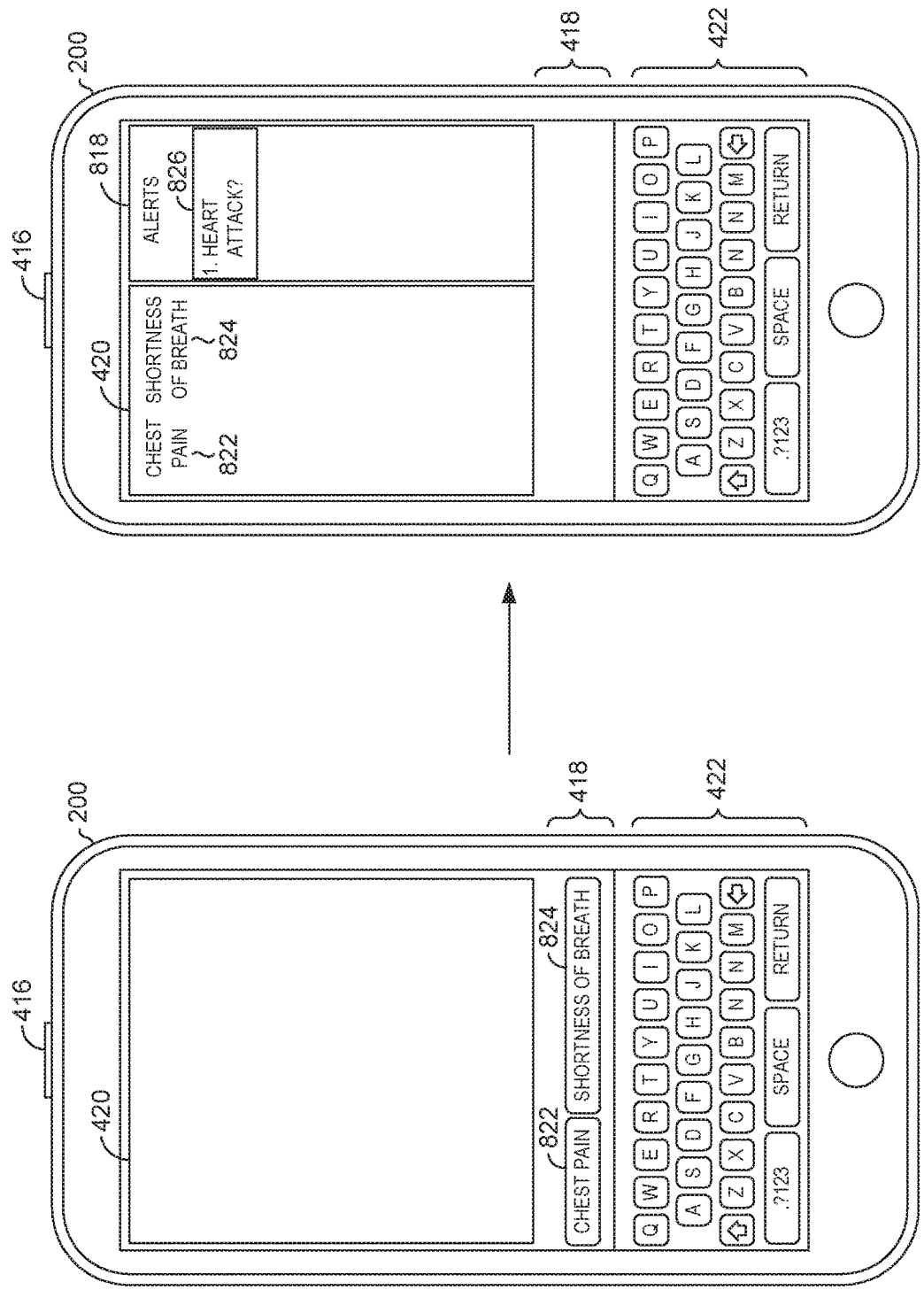

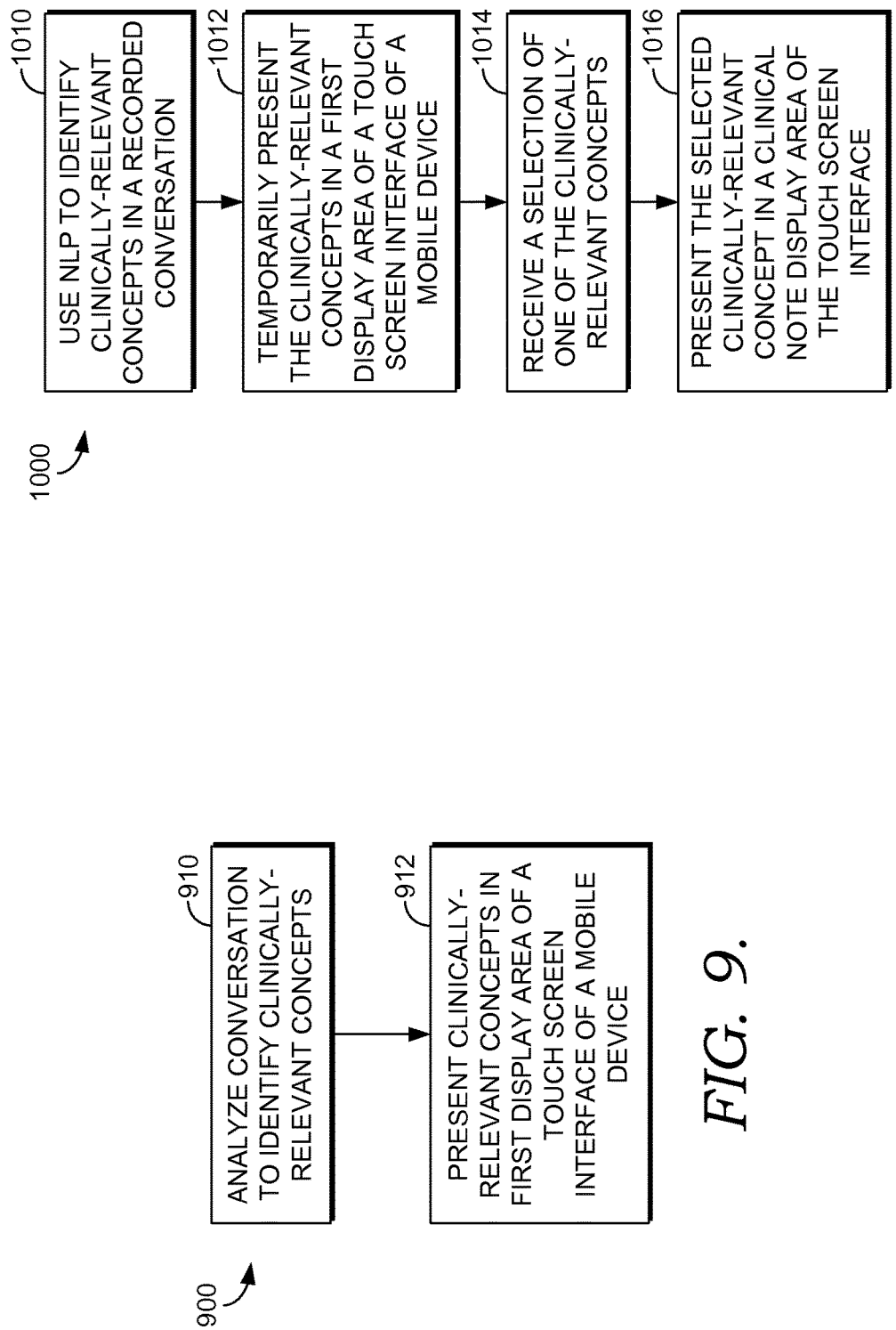

VOICE-ASSISTED CLINICAL NOTE CREATION ON A MOBILE DEVICE

BACKGROUND

Using a keypad on a mobile device or a tablet to capture clinical information spoken in a conversation between a clinician and a patient can be challenging since the keypads on these devices, whether physical or touch-screen, are generally quite compact in size and difficult to use. The clinician may spend more time attending to the keypad than attending to the actual conversation. The limitations imposed by these compact keypads may be partially overcome by utilizing predictive typing tools. These tools suggest words only as a user begins to manually input text using the keypad. Although this type of tool may be helpful in some situations, the suggested words typically are common words and do not include medical terms leaving the clinician the unenviable task of manually inputting complicated medical terminology using the keypad.

Voice dictation with subsequent transcribing is an alternative to inputting extensive information on mobile devices or tablets using a keypad. However, voice dictation is not practical in a situation where a clinician is speaking with a patient. The rapport between the patient and the clinician is compromised if the clinician is constantly interrupting the patient to dictate into a voice recorder.

Automatic speech recognition is yet another alternative, but these solutions typically transcribe the entire conversation between parties and require that a user go back and verify the content of the conversation and manually make any changes to misunderstood words. Although this may be useful in some situations, it may not be necessary if a clinician is simply wishing to capture the important parts of a conversation at the time they are spoken in order to generate a shorthand clinical note that may be used as a memory aid for the later generation of a more comprehensive clinical note.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for utilizing natural language processing (NLP) to facilitate the voice-assisted creation of a shorthand clinical note on a mobile device or tablet. A microphone associated with the mobile device or tablet captures an ongoing conversation between, for example, a patient and a clinician. The conversation is analyzed using natural language processing to identify clinically-relevant concepts as they are spoken. The identified concepts are temporarily presented on the device's touch screen interface. The clinician can then select one or more of the presented concepts, and the selected concepts are populated into a shorthand clinical note on the touch screen interface. The shorthand clinical note can then be used as a memory aid for the clinician when generating a more comprehensive clinical note that can be stored in, for instance, the patient's electronic medical record (EMR).

The methods described above enable the clinician to closely attend to what the patient is saying without being distracted by excessive typing and/or voice dictation. In addition, the ability to create a shorthand clinical note by identifying clinically-relevant concepts at the time they are spoken in a conversation and presenting just these concepts provides advantages over predictive typing and automatic speech recognition technologies.

BRIEF DESCRIPTION OF THE DRAWINGS

Embodiments are described in detail below with reference to the attached drawings figures, wherein:

FIGS. 4A-4E illustrate capturing an exemplary ongoing conversation between a clinician and a patient and the presenting clinically-relevant concepts identified from the conversation on a touch screen interface of a mobile device according to embodiments of the present invention;

FIGS. 5A-5B illustrate the presentation of exemplary modifiers on a touch screen interface of mobile device, where the exemplary modifiers may be used to modify clinically-relevant concepts identified from a conversation between a patient and a clinician according to embodiments of the present invention;

FIGS. 6A-6B illustrate the presentation of a suggested problem list that is related to a clinically-relevant concept identified from a conversation between a patient and a clinician according to embodiments of the present invention;

FIGS. 7A-7B illustrate the presentation of an order set that is related to a clinically-relevant concept identified from a conversation between a patient and a clinician according to embodiments of the present invention;

FIGS. 8A-8B illustrate the presentation of alerts that are related to one or more clinically-relevant concepts identified from a conversation between a patient and a clinician according to embodiments of the present invention;

FIG. 9 depicts a flow diagram of an exemplary method of utilizing natural language processing to identify clinically-relevant concepts spoken in a conversation between a clinician and a patient and the presentation of the identified concepts on a touch screen interface of a mobile device according to an embodiment of the present invention; and FIG. 10 depicts a flow diagram of an exemplary method of utilizing natural language processing to generate a shorthand clinical note on a touch screen interface of a mobile device according to an embodiment of the present invention.

DETAILED DESCRIPTION

Figure 1:
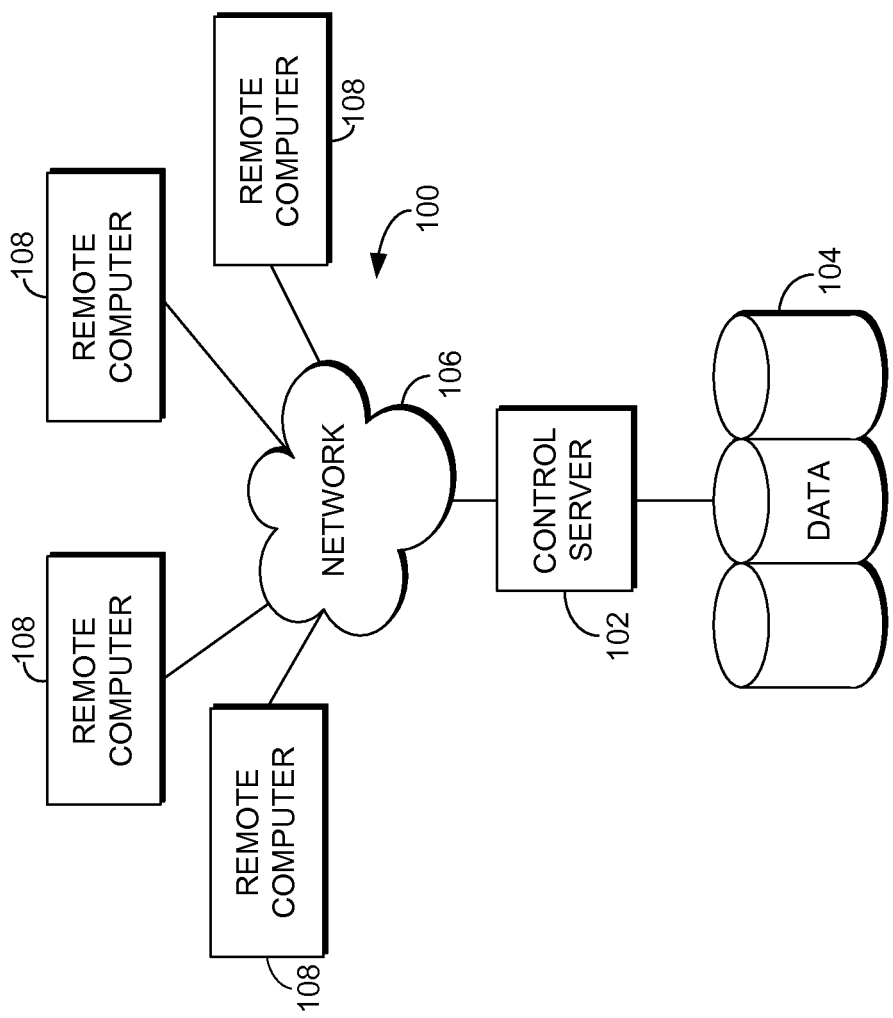
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for utilizing a microphone associated with a mobile device or tablet to capture an ongoing conversation spoken between two users, and using natural language processing to identify relevant concepts as they are spoken in the conversation. The relevant concepts are then temporarily presented on a touch screen interface of the mobile device or tablet. The concepts are selectable, and upon selection the selected concept is populated into a shorthand note display area of the mobile device. As new relevant concepts are identified and extracted from the conversation, existing relevant concepts that were not selected are replaced with the new concepts. The user of the mobile device can input additional text using, for example, the device's keypad to supplement the concepts in the shorthand note display area. Using the described process, the user can quickly create a shorthand note with minimal keystrokes. The shorthand note may be used in some instances to aid in the creation of a more comprehensive note or document.

Embodiments of the present invention may be configured for use in a wide variety of settings such as a financial setting, a legal setting, a medical setting, or other types of industry-specific settings. In each of these settings, a unique set of rules may be utilized to identify industry-specific relevant terms. For instance, in a financial setting, the conversation may take place between a financial advisor and his or her client. The relevant terms may comprise financial terms or numbers that are used in the creation of a shorthand note on the advisor's mobile device. The shorthand note then may be used as the basis for a financial summary document provided to the client at a later point in time. In a legal setting, the conversation may take place between a lawyer and his or her client. In this setting, the relevant terms may comprise legal terms that are used in the creation of a shorthand note on the lawyer's tablet device; the note then may be the basis for, for instance, a litigation proposal provided by the lawyer to the client. One setting of particular note is a clinical setting where a clinician meets with a patient to discuss the patient's health. These discussions typically involve clinically-related terms that are useful in the creation of a shorthand clinical note on the clinician's device as will be explained in greater depth below. The shorthand clinical note may be used as a memory aid to the clinician when the clinician is generating a comprehensive clinical note that will be stored in the patient's EMR.

In the context of a clinical setting, the present invention contemplates aspects in addition to the identification and extraction of clinically-relevant concepts as they are spoken and the presentation of these concepts on a touch screen interface of a mobile device or tablet. For example, in one aspect a list of pre-generated modifiers or dynamically generated modifiers may also be presented on the touch screen interface. Before or after selecting a clinically-relevant concept, the clinician can select a modifier to add the modifier to the clinical note display area. As an example, the clinician may select the clinically-relevant concept, "Strep." This term is then added to the clinical note display area. The clinician can then select a modifier, such as the modifier "rule out" from the modifier list, and the selected modifier is then populated into the clinical note display area. Accordingly, the phrase in the clinical note display area may comprise "Strep—rule out." This shorthand note may later serve as a prompt to the clinician to, for instance, initiate an order for a Strep test.

In another aspect, once a particular clinically-relevant concept or concepts such as "burning" and "urination" are identified, a "Suggested Problem" list may be automatically generated and presented on the device's touch screen interface. The Suggested Problem list may include several possible diagnoses related to the clinically-relevant concepts, "burning" and "urination." For example, the list may include diagnoses such as dehydration, urinary tract infection, and the like. The clinician can select one of these possible diagnoses, and the selected diagnosis is automatically added to the patient's problem list in the patient's EMR.

In an additional aspect, upon identifying a particular clinically-relevant concept(s), a set of orders related to the selected concept(s) may be automatically generated and presented on the touch screen interface. The clinician has the option of selecting one of the orders to initiate the order. As an example, the clinically-relevant concepts, "burning" and "urination" may have been identified, and an order set that includes orders such as "Bactrim," "urinalysis," and/or "hydration" may be generated and presented on the touch screen interface. The clinician can initiate one or more of the presented orders by selecting a desired order(s).

In yet another aspect, upon identification of one or more clinically-relevant concepts, one or more alerts related to the selected concepts may be automatically generated and presented on the touch screen interface. For example, the clinically-relevant concept "chest pain" may be identified, and alerts such as "possible heart attack?" may be generated and presented on the touch screen interface. These alerts may act to cue the clinician to possible concerns related to the patient.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keypad, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
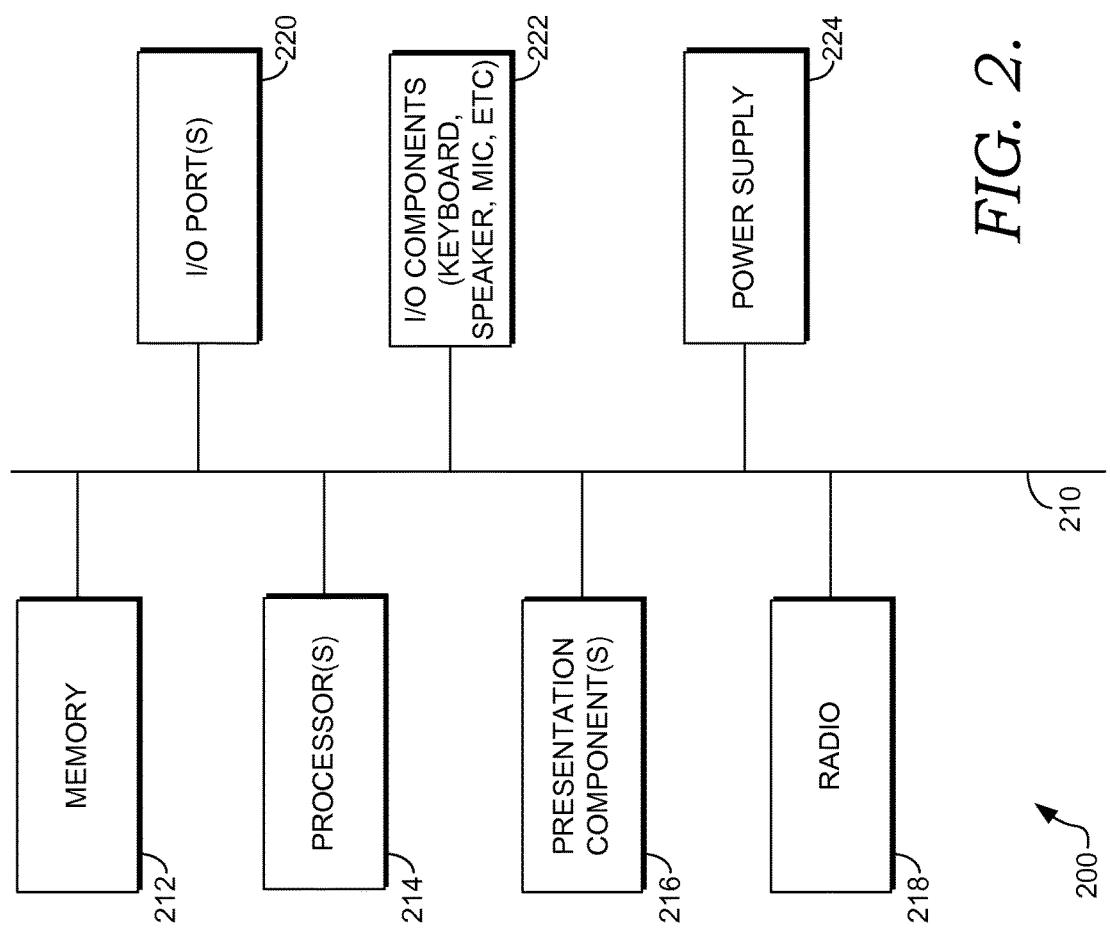
FIG. 2 depicts an exemplary mobile or tablet device suitable to implement embodiments of the present invention.

Turning now to FIG. 2, a block diagram of an illustrative mobile device or tablet device is provided and is referenced generally by the numeral 200. As used throughout this disclosure, the terms mobile device and tablet device are meant to encompass a wide variety of portable computing devices such as mobile phones, tablets, smart phones, notepads, notebooks, laptops, PDAs, wearable computers, and the like. Although some components are shown in the singular, they may be plural. For example, the mobile device 200 might include multiple processors or multiple radios, etc. As illustratively shown, the mobile device 200 includes a bus 210 that directly or indirectly couples various components together including memory 212, a processor 214, a presentation component 216, a radio 218, input/output ports 220, input/output components 222, and a power supply 224.

The memory 212 might take the form of memory components previously described. Thus, further elaboration will not be provided here, only to say that the memory component 212 can include any type of medium that is capable of storing information (e.g., a database). A database can be any collection of records. In one embodiment, the memory 212 includes a set of embodied computer-executable instructions that, when executed, facilitates various aspects disclosed herein. These embodied instructions will variously be referred to as "instructions" or an "application" for short.

The processor 214 might actually be multiple processors that receive instructions and process them accordingly. The presentation component 216 includes the likes of a display, a speaker, a touch screen interface, as well as other components that can present information.

The radio 218 facilitates communication with a wireless-telecommunications-network. Illustrative wireless-telecommunications technologies include CDMA, EvDO, GPRS, TDMA, GSM, WiMax technology, LTE, LTE Advanced and the like. In some embodiments, the radio 218 might also facilitate other types of wireless communications including Wi-Fi®, Bluetooth® communications, GIS communications, and other near-field communications.

The input/output port 220 might take on a variety of forms. Illustrative input/output ports include a USB jack, stereo jack, infrared port, proprietary communications ports, and the like. The input/output components 222 include items such as keypads, microphones, speakers, touch screens, and any other item usable to directly or indirectly input data into the mobile device 200. The power supply 224 includes items such as batteries, fuel cells, or any other component that can act as a power source to power the mobile device 200.

Figure 3:
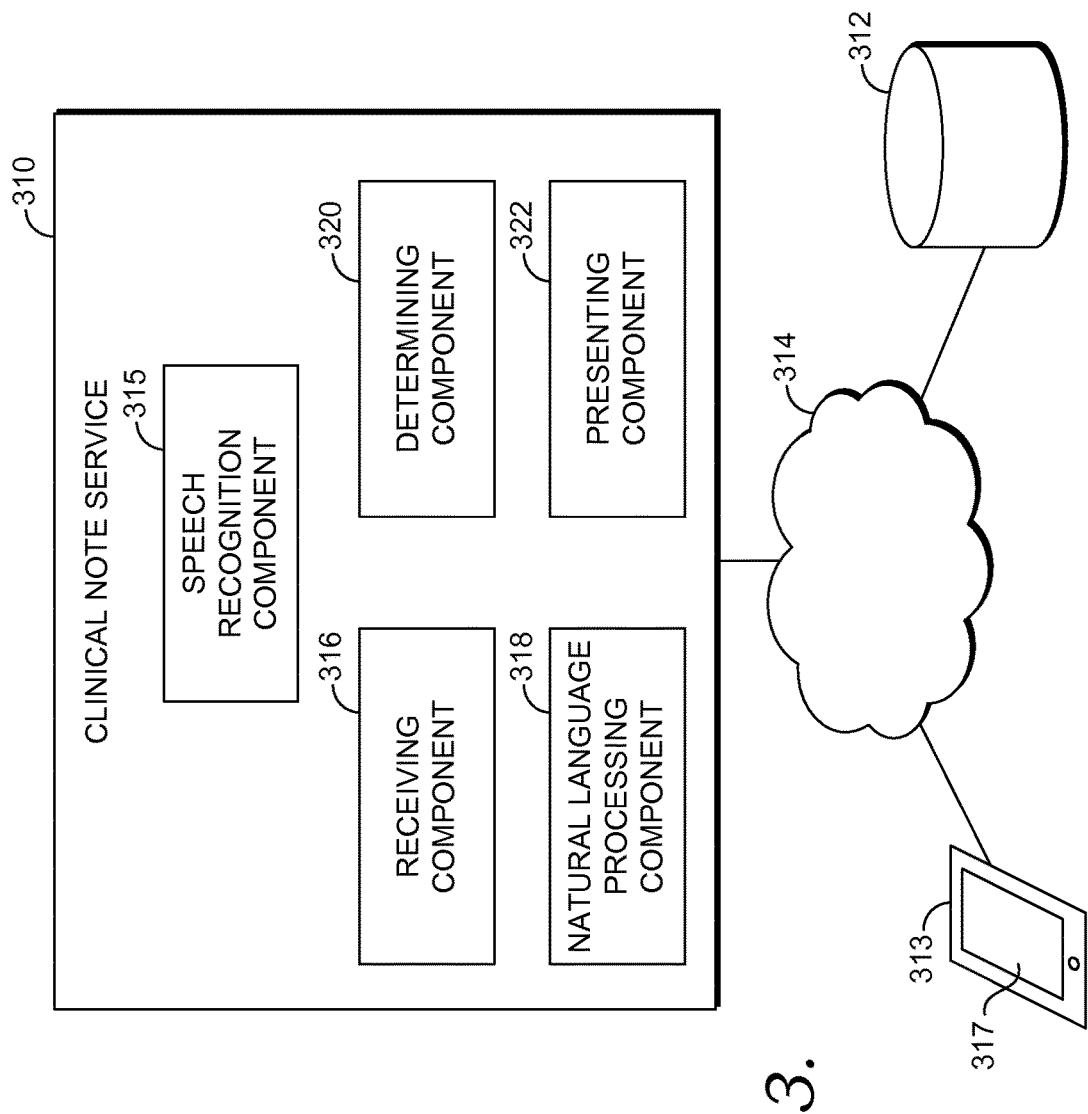
FIG. 3 is a block diagram of an exemplary computing system suitable to implement embodiments of the present invention.

Turning now to FIG. 3, an exemplary computing system environment 300 is depicted suitable for use in implementing embodiments of the present invention. The computing system environment 300 is merely an example of one suitable computing system environment and is not intended to suggest any limitation as to the scope of use or functionality of embodiments of the present invention. Neither should the computing system environment 300 be interpreted as having any dependency or requirement related to any single module/component or combination of modules/components illustrated therein.

The computing system environment 300 includes a clinical note service 310, a data store 312, and an end-user computing device 313, all in communication with each other via a network 314. The network 314 may include, without limitation, one or more local area networks (LANs) or wide area networks (WANs). Such networks are commonplace and, as such, will not be further described herein.

In some embodiments, one or more of the illustrated components/modules may be implemented as stand-alone applications. In other embodiments, one or more of the illustrated components/modules may be integrated directly into the operating system of the clinical note service 310. Moreover, the clinical note service 310 may be integrated directly into the operating system of the end-user computing device 313. The components/modules illustrated in FIG. 3 are exemplary in nature and in number and should not be construed as limiting. Any number of components/modules may be employed to achieve the desired functionality within the scope of embodiments hereof. Further, components/modules may be located on any number of servers. By way of example only, the clinical note service 310 might reside on a server, a cluster of servers, or a computing device remote from one or more of the remaining components.

The computing system environment 300 is merely exemplary. While the clinical note service 310 is illustrated as a single unit, it will be appreciated that the clinical note service 310 is scalable. For example, the clinical note service 310 may in actuality include a plurality of computing devices in communication with one another. Moreover, the data store 312, or portions thereof, may be included within, for instance, the clinical note service 310 as a computer-storage medium. The single unit depictions are meant for clarity, not to limit the scope of embodiments in any form.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 312 is configured to store information for use by, for example, the clinical note service 310. The information stored in association with the data store 312 is configured to be searchable for one or more items of information stored in association therewith. The information stored in association with the data store 312 may comprise general information used by the clinical note service 310

The data store 312 may store a variety of information. In an exemplary aspect, the data store may store clinically-relevant concepts, lists of modifiers, differential diagnoses lists, as well as standards-of-care and/or best practices as promulgated by specific healthcare facilities and/or by state or nationally-recognized governing bodies. The standards-of-care and/or best practices may be utilized, for example, when generating possible orders sets or alerts.

In one aspect, the data store 312, or a different data store, may store EMRs of patients associated with a healthcare facility. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, patient-entered information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The content and volume of such information in the data store 312 are not intended to limit the scope of embodiments of the present invention in any way. Further, though illustrated as a single, independent component, the data store 312 may, in fact, be a plurality of storage devices, for instance, a database cluster, portions of which may reside on the clinical note service 310.

As shown, the end-user computing device 313 includes a display screen 317. The display screen 317 is configured to display information to the user of the end-user computing device 313, for instance, information relevant to conversations between a clinician and a patient. Embodiments are not intended to be limited to visual display but rather may also include audio presentation, combined audio/visual presentation, and the like. The end-user computing device 313 may be any type of display device suitable for presenting a touch screen interface. Such computing devices may include, without limitation, a computer, such as, for example, any of the remote computers 108 described above with reference to FIG. 1. Other types of display devices may include tablet PCs, PDAs, mobile phones, and smart phones, such as the mobile or tablet device 200 of FIG. 2. Interaction with the touch screen interface may be via a touch pad, a microphone, a pointing device, and/or gestures.

As shown in FIG. 3, the clinical note service 310 comprises a speech recognition component 315, a receiving component 316, a natural language processing component 318, a determining component 320, and a presenting component 322. In some embodiments, one or more of the components 315, 316, 318, 320, and 322 may be implemented as stand-alone applications. In other embodiments, one or more of the components 315, 316, 318, 320, and 322 may be integrated directly into the operating system of a computing device such as the mobile device 200 of FIG. 2 or the end-user computing device 313. It will be understood that the components 315, 316, 318, 320, and 322 illustrated in FIG. 3 are exemplary in nature and in number and should not be construed as limiting. Any number of components may be employed to achieve the desired functionality within the scope of embodiments hereof.

The speech recognition component 315 is configured to take an audio feed captured by a microphone and convert the audio feed into a text stream. Moreover, the speech recognition component 315 performs this function substantially simultaneously with when the words are spoken. Additionally, the speech recognition component 315 may be configured to analyze voice profiles captured in the audio feed and compare the profiles to know voice profiles stored in association with, for example, the data store 312. In this way, the speech recognition component 315 may create associations between a particular audio feed and/or text stream and a particular user. In an illustrative example, the data store 312 may store voice profiles for a variety of clinicians. The speech recognition component 315 may match a particular audio feed to a particular clinician and thereby create an association between the text stream of the audio feed and the particular clinician.

The receiving component 316 is configured to receive a variety of inputs. For example, the receiving component 316 is configured to receive user selections, such as selections of clinically-relevant concepts that are displayed on the mobile device's touch screen interface. Other user selections may include the selection of one or more modifiers, the selection of one or more order sets, the selection of an option designating a word as being spoken by a clinician or a patient, the selection of possible diagnoses, and the like. The selections may be initiated by the user using gestures (touching, tapping, or swiping), a stylus, voice, and the like. The receiving component 316 is further configured to receive user-inputted text streams. For instance, the user may input a text stream using the device's keypad. The receiving component 316 is additionally configured to receive information stored in association with the data store 312. The information may include, for example, clinically-relevant concepts, modifier lists, voice profiles, differential diagnoses lists, orders sets, alerts, and the like.

The natural language processing component 318 is configured to apply natural language processing to the text stream from the captured conversation in order to identify clinically-relevant concepts. One exemplary natural language processing technology is Cerner Discern nCode™ developed by Cerner® Corporation in Kansas City, Mo. Clinically-relevant concepts may comprise terminology describing symptoms, tests, results, conditions, procedures, orders, medications, anatomy, and the like. Additionally, clinically-relevant concepts may comprise dates, numbers, and units of measurement (e.g., grams, milligrams, inches, centimeters, and the like), as these may modify or provide additional context to the terminology describing the symptoms, conditions, procedures, tests, results, orders, medications, and anatomy.

In one aspect, the natural language processing component 318 analyzes each word, group of words, numbers, or dates (hereinafter collectively known as "words") in the conversation to determine if the words comprise a clinically-relevant concept. This may be done by applying a set of rules to the words. In one aspect, the natural language processing component 318 is configured to identify clinically-relevant concepts that match or substantially match the words in the conversation. For example, the spoken phrase may comprise, "burning on urination," and the natural language processing component 318 identifies clinically-relevant concepts that match or substantially match this phrase. For instance, the clinically-relevant concepts in this case may comprise "burning" and "urination." In another aspect, the natural language processing component 318 may perform processing on the spoken words to identify a clinically-relevant concept that matches the general meaning of the spoken words. Thus, with the spoken phrase, "burning on urination," the natural language processing component 318 may determine that this phrase corresponds to the clinically-relevant concept of "dysuria." Any and all such aspects, and any variation thereof, are contemplated as being within the scope of the invention. The natural language processing component 318 carries out its determinations substantially simultaneously (e.g., in near real-time) as the words are spoken by a user or users and converted to text by the speech recognition component 315.

The natural language processing component 318 is further configured to analyze conversation patterns in order to identify who is speaking (e.g., the clinician or the patient). For example, clinicians may naturally have conversation patterns that utilize a greater number of clinically-relevant terms as compared to patients. Or, in another example, clinicians may have conversation patterns that include more questions as compared to statements. By analyzing the conversation pattern, the natural language processing component 318 may make a best-guess effort as to who is speaking at any one time.

The determining component 320 configured to automatically determine suggested problem lists, orders sets, and/or alerts that relate or correspond to one or more of the clinically-relevant concepts. The determining component 320 may utilize differential diagnoses lists, standards-of-care, and/or best practices stored in association with the data store 312 when making its determinations. In an exemplary aspect, the determinations may occur at substantially the same time as when a clinically-relevant concept is identified, or at substantially the same time as when a user actually selects a concept such that the concept is populated into a clinical note display area on the device. Selection of a concept indicates that the clinician believes that the concept is particularly relevant and by waiting until the user actually selects a concept, processing power may be saved until needed. Moreover, in an exemplary aspect, the determination may only be initiated if the identified and/or selected clinically-relevant concept comprises a symptom, a set of symptoms, or a diagnosis. For example, the determining component 320 may not make a determination when the identified or selected clinically-relevant concept comprises a date or a number.

The presenting component 322 is configured to display clinically-relevant concepts, modifier lists, suggested problem lists, alerts, and/or order sets on a touch screen interface of the mobile device. In one aspect, the presenting component 322 may be configured to present identified concepts temporarily in a first display area of the touch screen interface. The first display area may be located adjacent to a keypad associated with the device. The concepts may be presented in the first display area in the order in which the words are spoken in the conversation. In a first aspect, the concepts may be presented for a predetermined period of time such as one second, two seconds, three seconds, four seconds, or five seconds. If the concept is not selected within this predetermined period of time, the presenting component 322 removes the concept from the touch screen interface such that it is no longer presented. In a second aspect, the concepts may be presented until a predetermined number of new concepts are identified. Upon identifying the predetermined number of new concepts, the "older" concepts may be removed from the first display area and replaced with the new concepts. Any and all such aspects, and any variation thereof, are contemplated as being within the scope herein.

If a clinically-relevant concept in the first display area is selected, the presenting component 322 is further configured to populate the selected concept into a clinical note display area of the touch screen interface. This display area may be located, for example, adjacent to the first display area. The presenting component 322 populates the selected concepts into the clinical note display area in the order in which they are selected. Once the clinically-relevant concept is populated into the clinical note display area, the presenting component 322 may be configured to present an option that allows the user to tag a particular concept as having been spoken by the clinician or by the patient. For example, once the selected concept is populated into the clinical note display area, a user may tap the concept and be presented with a "clinician" option or a "patient" option. By selecting one of the options, the user can associate the concept with having been spoken by either the clinician or the patient. This may be useful when the clinician later reviews the shorthand note and wants to refresh him or herself as to who spoke a particular word.

The presenting component 322 may also be configured to present a list of modifiers in a modifier display area located adjacent to the clinical note display area and/or the first display area. The presentation of modifiers may be dependent upon specified user preferences. For example, the user may explicitly indicate that he or she always wants the modifier list presented when creating the shorthand clinical note. In another aspect, the user may utilize a specified function to initiate, or disable, the display of the modifier list. For example, the user may tap the area of the touch screen interface where the modifier list is typically presented in order to initiate and/or disable the presentation of the modifier list, or the user may enter a certain key on the keypad to initiate and/or disable the presentation of the modifier list. In yet another aspect, the presentation of the modifier list may be based on usage patterns of the user. For example, if the user rarely or never utilizes the modifier list, the presenting component 322 may no longer present the list. In still another aspect, the modifier list may be dynamically generated and presented upon determining that a particular set of modifiers is relevant to a particular identified concept. Any and all such aspects, and any variation thereof, are contemplated as being within the scope of the invention.

The presenting component 322 may additionally be configured to present an order set in an order set display area, a suggested problem list in a suggested problem list display area, and/or alerts in an alerts display area. As described above, the determination of order sets, suggested problem lists, and/or alerts is dependent upon identifying and/or selecting a clinically-relevant concept that comprises a symptom or set of symptoms, and/or a diagnosis. These display areas may also be located adjacent to the clinical note display area and/or the first display area for easy visual reference while the clinician is generating the shorthand clinical note. Depending on the amount of available screen real estate, one or more of the modifier list, the order set list, the suggested problem list, and/or the alerts may be presented at any one time. Users may specify a priority order for presentation. Further, the order set list, suggested problem list, and/or alerts may only be presented for a predetermined period of time starting when the relevant concept is populated into the clinical note display area. The predetermined period of time may comprise one second, two seconds, three seconds, four seconds, or five seconds.

Turning now to FIGS. 4A-4E, a series of illustrations are shown depicting an exemplary conversation between a clinician and a patient, the automatic identification of clinically-relevant concepts in the conversation, and the presentation of these concepts on a touch screen interface of a mobile device associated with the clinician. As used throughout this disclosure, the term "automatically" means without human intervention.

With respect to FIG. 4A, FIG. 4A depicts a clinician 410, a patient 412, and a mobile device 200. Although the mobile device depicted in these figures resembles a cellular phone, it is contemplated that the mobile device 200 may comprise a tablet, a laptop, and the like. The mobile device 200 includes a microphone 416 that is used to capture the conversation between the clinician 410 and the patient 412. The mobile device 200 further includes a keypad 422 which may be a physical keypad or a touch screen keypad. As well, the mobile device 200 includes a first display area 418 that is used to present clinically-relevant concepts that are identified from the conversation between the clinician 410 and the patient 412, and a shorthand clinical note display area 420 that is used to present concepts that have been selected by a user in the first display area 418. The first display area 418 may, in one aspect, be located in an area vertically above and adjacent to the keypad 422. Further, the clinical note display area 420 may be located vertically above and adjacent to the first display area 418. The location of these display areas is exemplary only. Other configurations are contemplated as being within the scope hereof.

As shown in FIG. 4A, the conversation between the clinician 410 and the patient 412 begins with the clinician 410 asking the patient 412 why the patient 412 is being seen. The patient 412 responds that she has been coughing and has had a sore throat. This exchange is captured by the microphone 416 and translated into text by a speech recognition component such as the speech recognition component 315 of FIG. 3. The terms "coughing" and "sore throat" are recognized by a natural language processing component (such as the natural language processing component 318 of FIG. 3) as being clinically-relevant concepts, and, accordingly, they are presented in the first display area 418 by a presenting component such as the presenting component 322 of FIG. 3—the clinically-relevant concept of "coughing" is shown at numeral 426 and the clinically-relevant concept of "sore throat" is shown at numeral 428. The clinically-relevant concepts 426 and 428 are presented in the order in which they were spoken in the conversation.

As illustrated in FIG. 4B, the clinician 410 has selected the clinically-relevant concept "sore throat" 428 by, for example, tapping or touching the concept "sore throat" 428, and the concept "sore throat" 428 is then populated into the shorthand clinical note display area 420. After the concept "sore throat" 428 has been selected, it is no longer displayed in the first display area 418. The clinician 410 has the option of using the keypad 422 to input additional information concerning, for example, the concept "sore throat" 428; the additional information is populated into the clinical note display area 420.

Once populated into the clinical note display area 420, the clinician 410 may select the concept "sore throat" 428 (e.g., by tapping the concept 428) to initiate the presentation of options to associate the concept "sore throat" 428 with having been spoken by the clinician 410 or the patient 412. The ability to associate a particular concept as having been spoken by the clinician 410 or the patient 412 provides important context to the clinician 410 when the clinician 410 is generating the comprehensive clinical note.

Other ways of associating a particular concept as having been spoken by the clinician 410 or the patient 412 are contemplated herein. For example, the concept "sore throat" 428 may automatically be associated with either the clinician 410 or the patient 412 based on matching a voice profile of the clinician 410 or the patient 412 captured when speaking the words "sore throat" with a known voice profile stored in association with, for example, the data store 312. In another example, natural language processing may be used to analyze the context in which the selected concept "sore throat" 428 was used in the conversation and to tag the concept "sore throat" 428 as being spoken by the clinician 410 or the patient 412 based on the conversation pattern.

In one aspect, the concept "coughing" 426 may continue to be presented for a predetermined period of time and, if not selected within this time, it is no longer presented as shown in FIG. 4B. The predetermined period of time may, in exemplary aspects, be one second, two seconds, three seconds, four seconds, or five seconds. Alternatively, the concept "coughing" 426 may continue to be presented in the first display area 418 until a predetermined number of additional clinically-relevant concepts are identified from the conversation. This predetermined number may be based on the amount of available screen space on the device 200. Although not selected, the concept "coughing" 426 may be stored in a data store such as the data store 312. In the event that it is deemed relevant at a future period of time, the concept "coughing" 426 can be retrieved from the data store and inserted into the clinical note display area 420.

Meanwhile, the conversation between the clinician 410 and the patient 412 continues in FIG. 4B with the clinician 410 asking the patient 412 if the patient 412 has had a fever and the patient 412 responding that she had a temperature of 103 degrees. The clinically-relevant concepts of "fever" and "103" are identified and presented in the first display area 418 as "fever" 430 and "103" 432. Again, the concepts "fever" 430 and "103" 432 are presented in the first display area 418 in the order in which they are spoken and are presented for either a predetermined period of time or until a predetermined number of additional clinically-relevant concepts are identified.

Figure 4C:
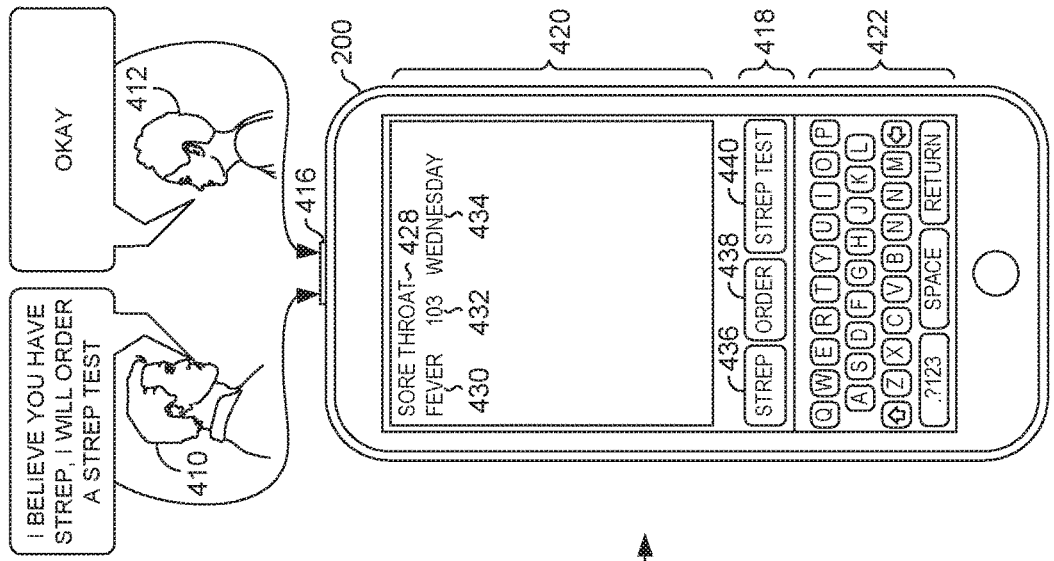

In FIG. 4C, the clinician 410 has selected both the concept "fever" 430 and the concept "103" 432, and these concepts are populated into the clinical note display area 420. The concepts 430 and 432 may be presented on the same line as the concept "sore throat" 428, or, as shown in FIG. 4C, the concepts 430 and 432 may be presented on a new line incident to the clinician 410 hitting the "enter" or "return" button on the keypad 422 after the concept "sore throat" 428 has been populated into the clinical note display area 420. Thus, by utilizing the enter or return function of the keypad 422, the clinician 410 can implicitly create associations between concepts which further aids the clinician 410 when he is generating a comprehensive clinical note at a later point in time.

As illustrated in FIG. 4C, the conversation between the clinician 410 and the patient 412 continues with the clinician 410 asking the patient 412 when she had the fever and the patient 412 replying that the fever was Wednesday night. Since the clinically-relevant concept of "fever" 430 has already been identified and presented in the first display area 418, it is not presented again. However, the clinically-relevant concept of "Wednesday" is identified and presented in the first display area 418 as the concept 434. The concept "Wednesday" 434 is relevant because it provides context for when the fever occurred.

Figure 4D:
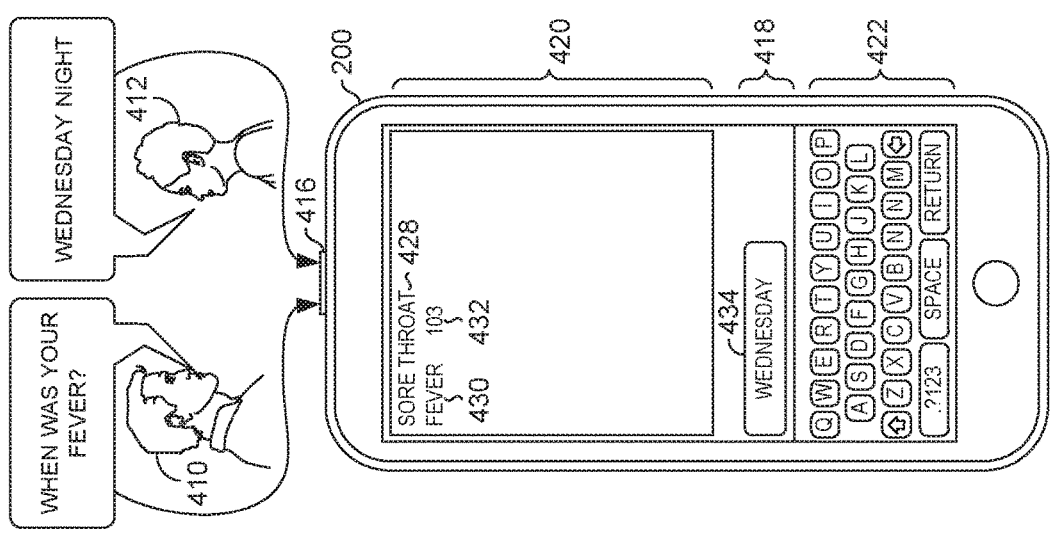

As shown in FIG. 4D, the clinician 410 has selected the concept "Wednesday" 434, and the concept 434 has been populated into the clinical note display area 420. The clinician 410 has elected to populate the concept "Wednesday" 434 on the same line as the concepts "fever" 430 and "103" 432 to provide further context to when the fever occurred. FIG. 4D further depicts the ongoing conversation between the clinician 410 and the patient 412 with the clinician 410 informing the patient 412 that he believes the patient 412 has Strep, and that the clinician 410 would like to order a Strep test. The clinically-relevant concepts of "Strep," "order," and "Strep test" are identified and are presented in the first display area as the concepts "Strep" 436, "order" 438, and "Strep test" 440. As shown, the first display area 418 is adapted to present multiple words at any given time depending on the amount of screen real estate available on the touch screen interface of the mobile device 200.

Figure 4E:
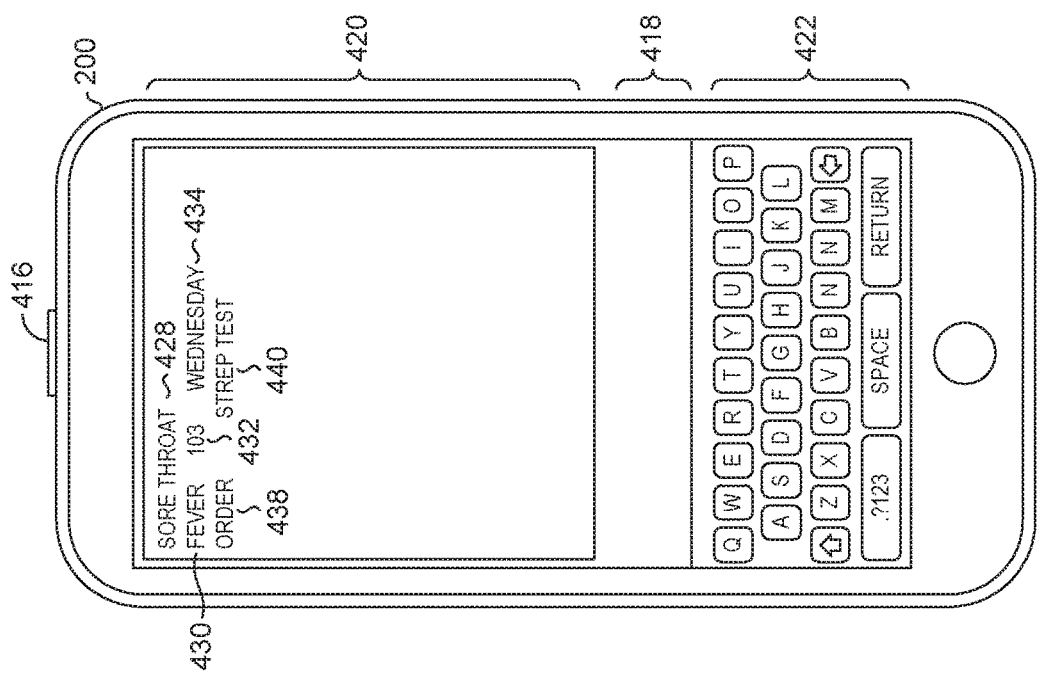

FIG. 4E illustrates that the clinician 410 has opted to select the concepts "order" 438 and "Strep test" 440 but not the concept "Strep" 436. Because the concept "Strep" 436 was not selected, it is no longer presented in the first display area 418. The selected concepts 438 and 440 are populated into the clinical note display area 420 on a new line (incident to the clinician 410 executing an enter or return function). The shorthand clinical note displayed in the clinical note display area 420 may be used by the clinician 410 as a memory aid when the clinician 410 is generating a more comprehensive clinical note summarizing the patient encounter.

Turning now to FIGS. 5A-5B, a mobile device 200 is depicted at two points in time. Like the mobile device 200 of FIGS. 4A-4E, the mobile device 200 includes a microphone 416 for capturing conversations, a first display area 418 for temporarily presenting clinically-relevant concepts identified and extracted from the conversation, a keypad 422 for inputting text, and a clinical note display area 420 for displaying clinically-relevant concepts that have been selected by a user in the first display area 418. As shown in FIG. 5A, the first display area 418 currently is presenting a clinically-relevant concept "Strep" 436 that has been identified and extracted from a conversation between, for instance, a clinician and a patient. And as shown in FIG. 5B, the concept "Strep" 436 has been selected and is now populated into the clinical note display area 420.

The mobile device 200 of FIG. 5A further includes a modifier list 518 that is displayed in an area adjacent to the clinical note display area 420 and the first display area 418. In exemplary aspects, the modifier list 518 may be presented to the left or the right of the clinical note display area 420. In other exemplary aspects, the modifier list 518 may be presented above and adjacent of the clinical note display area 420. Moreover, upon presentation of the modifier list 518, the clinical note display area 420 may be reduced in size to accommodate the modifier list 518. Any and all such aspects, and any variation thereof, are contemplated as being within the scope of the invention.

The modifier list 518 may include, in one aspect, a list of predefined or pre-generated modifiers. Exemplary modifiers may include, for example, no, yes, positive, negative, rule-out, contraindicated, and the like. As well, the modifiers may be abbreviated to decrease the amount of screen real estate taken up by the modifier list 518 (e.g., "y" for yes, "n" for no, "R/U" for rule-out, and so on). The modifiers are selectable, and upon selection, the selected modifier is populated into the clinical note display area 420. For example, as shown in FIG. 5B, the modifier "R/U" 524 has been selected and has been populated into the clinical note display area 420 where it modifies the clinically-relevant concept "Strep" 436. Unlike the clinically-relevant concepts presented in the first display area 418, a particular modifier may continue to be shown in the modifier list 518 even after selection.

In addition to predefined or pre-generated modifier lists, it is contemplated that modifiers may be generated and presented dynamically or on-the-fly. For instance, a particular set of modifiers may be determined by a determining component, such as the determining component 320 of FIG. 3, to be relevant to a particular clinically-relevant concept; the determined modifiers may then be presented in the modifier list 518. As an illustrative example, the clinically-relevant concept "Strep" may be identified and/or selected, and a set of modifiers may be dynamically generated that includes "yes," "no," and "rule-out." In another example, the clinically-relevant concept "digoxin" may be identified and/or selected, and a set of modifiers may be dynamically generated that includes "yes," "no," and "contra-indicated."

With respect to FIGS. 6A-6B, these figures illustrate the dynamic presentation of a suggested problem list upon determining that it may be relevant to a particular identified and/or selected concept. FIGS. 6A-6B depict a mobile device 200 having a microphone 416, a first display area 418, a clinical note display area 420, and a keypad 422. The first display area 418 in FIG. 6A is currently presenting the clinically-relevant concepts "burning" 622 and "urination" 624 identified and extracted from a conversation between a clinician and a patient. FIG. 6B illustrates that the concepts 622 and 624 have been selected and populated into the clinical note display area 420. FIG. 6B further illustrates that a suggested problem list 618 has been generated and displayed alongside the clinical note display area 420. The suggested problem list 618, in exemplary aspects, may be displayed to the right or to the left of the clinical note display area 420. Moreover, upon presentation of the suggested problem list 618, the clinical note display area 420 may be reduced in size to accommodate the suggested problem list 618.

The suggested problem list 618 may be presented incident to a determination that it is relevant to the clinically-relevant concepts "burning" 622 and "urination" 624; the determination may be carried out by a determining component such as the determining component 320 of FIG. 3. The suggested problem list 618 includes a list of possible diagnoses related to the concepts "burning" 622 and "urination" 624. In this case, the exemplary diagnoses include UTI (urinary tract infection) 628, dehydration 630, and allergic reaction 632. Abbreviations may be used when presenting the diagnoses to minimize the amount of screen real estate occupied by the problem list 618. As well, the individual diagnoses may be numbered.

The user of the mobile device 200 has the option of selecting one or more of the possible diagnoses 628, 630, and/or 632. Selection may occur via the user touching or tapping one of the diagnoses, by the user speaking one or more of the diagnoses, and/or by the user speaking or selecting the number associated with the diagnosis (e.g., the numbers "1," "2," and/or "3"). Once selected by the user, the selected diagnosis may be added to the patient's problem list in the patient's EMR.

In exemplary aspects, the suggested problem list 618 may be presented for a predetermined period of time such as one second, two seconds, three seconds, four seconds, or five seconds. If a diagnosis is not selected within the predetermined period of time, the suggested problem list 618 is no longer displayed on the touch screen interface of the mobile device 200. In another exemplary aspect, the suggested problem list 618 may be presented until a new clinically-relevant concept is identified and/or populated into the clinical note display area 420. Incident to this occurrence, a new suggested problem list that may be relevant to the new concept may be generated and presented.

FIGS. 7A-7B illustrate the dynamic presentation of an order list upon determining that it is relevant to one or more identified and/or selected concepts. FIGS. 7A and 7B depict a mobile device 200 having microphone 416 to capture a conversation, a first display area 418 for displaying clinically-relevant concepts identified and extracted from the conversation, a keypad 422, and a clinical note display area 420 for presenting clinically-relevant concepts that have been selected by a user while being displayed in the first display area 418. For instance, as shown in FIG. 7A, the clinically-relevant concepts of "burning" 622 and "urination" 624 are presented in the first display area 418, and as shown in FIG. 7B, these concepts have been selected and are populated into the clinical note display area 420.

FIG. 7B illustrates that an order list 718 that has been generated and displayed alongside the clinical note display area 420. The order list 718, in exemplary aspects, may be displayed to the right or to the left of the clinical note display area 420. Moreover, upon presentation of the order list 718, the clinical note display area 420 may be reduced in size to accommodate the order list 718.

The order list 718 may be presented incident to a determination that it is relevant to, for example, the clinically-relevant concepts "burning" 622 and "urination" 624; the determination may be carried out by a determining component such as the determining component 320 of FIG. 3. The order list 718 includes a list of possible order sets related to the concepts "burning" 622 and "urination" 624. Because these concepts indicate a possible urinary tract infection, an exemplary order set may include Bactrim 726 (a common antibiotic used to treat urinary tract infections), and UA (urinalysis) 728. Abbreviations may be used when presenting the orders to minimize the amount of screen real estate occupied by the order list 718. As well, each of the orders may be numbered.

The user of the mobile device 200 has the option of selecting one of the possible orders 726 and/or 728. Selection may occur via the user touching or tapping one of the diagnoses, by the user speaking one or more of the diagnoses, and/or by the user speaking or selecting the number associated with the order (e.g., the numbers "1," and/or "2"). More than one order may be selected. Once selected by the user, the selected order(s) may be stored in the patient's EMR and/or initiated.

In exemplary aspects, the order list 718 may be presented for a predetermined period of time such as one second, two seconds, three seconds, four seconds, or five seconds. If an order is not selected within the predetermined period of time, the order list 718 may no longer displayed on the touch screen interface of the mobile device 200. In another exemplary aspect, the order list 718 may be displayed until a new clinically-relevant concept is identified and/or populated into the clinical note display area 420. Incident to identifying a new clinically-relevant concept, a new order list may be generated and presented thereby replacing the existing order list. The order list 718, in exemplary aspects, may be presented in association with a suggested problem list such as the suggested problem list 618 of FIG. 6B depending on the amount of available screen real estate on the mobile device 200, and/or depending on whether both are relevant to the identified and/or selected clinically-relevant concept(s).

FIGS. 8A-8B illustrate the dynamic presentation of an alert list upon determining that it is relevant to one or more identified and/or selected concepts. FIGS. 8A and 8B depict a mobile device 200 having microphone 416 to capture a conversation, a first display area 418 for displaying clinically-relevant concepts identified and extracted from the conversation, a keypad 422, and a clinical note display area 420 for presenting clinically-relevant concepts that have been selected by a user while being displayed in the first display area 418. For instance, as shown in FIG. 8A, the clinically-relevant concepts of "chest pain" 822 and "shortness of breath" 824 are presented in the first display area 418 based on their identification and extraction from a conversation between a clinician and a patient. As shown in FIG. 8B, these concepts have been selected and are populated into the clinical note display area 420.

FIG. 8B illustrates that an alert list 818 has been generated and displayed alongside the clinical note display area 420. The alert list 818, in exemplary aspects, may be displayed to the right or to the left of the clinical note display area 420. Moreover, upon presentation of the alert list 818, the clinical note display area 420 may be reduced in size to accommodate the alert list 818.

The alert list 818 may be presented incident to a determination that it is relevant to, for instance, the clinically-relevant concepts "chest pain" 822 and "shortness of breath" 824; the determination may be carried out by a determining component such as the determining component 320 of FIG. 3. The alert list 818 includes a list of one or more alerts related to the concepts "chest pain" 822 and "shortness of breath" 824. In this case, the alert comprises "heart attack?" 826 and is presented to act as a prompt to the clinician to consider this diagnosis because early intervention significantly reduces the morbidity and mortality associated with this condition. Abbreviations may be used when presenting the alerts to minimize the amount of screen real estate occupied by the alert list 818. As well, the list may be numbered.

Other alerts are contemplated as being within the scope hereof. For example, if the identified and/or selected clinically-relevant concept(s) indicates a possible food poisoning scenario, contagious disease scenario, or the like, the alerts may comprise bio surveillance alerts such as "Hepatitis A outbreak?," "typhus outbreak?," and the like. These alerts may prompt the clinician to contact, for example, local health agencies who may conduct further investigation.

The user of the mobile device 200 has the option of selecting the alert 826. Selection may occur via the user touching or tapping the alert, by the user speaking the alert, and/or by the user speaking or selecting the number associated with the alert (e.g., the number "1"). Once selected by the user, the alert is flagged in the patient's EMR so that the clinician can promptly act on it.

In exemplary aspects, the alert list 818 may be presented for a predetermined period of time such as one second, two seconds, three seconds, four seconds, or five seconds. If an alert is not selected within the predetermined period of time, the alert list 818 may no longer displayed on the touch screen interface of the mobile device 200. In other exemplary aspects, the alert list 818 may be displayed until new clinically-relevant concepts are identified and/or selected and populated into the clinical note display area 420. Incident to identifying and/or selecting a new clinically-relevant concept, a new alert list may be generated and presented thereby replacing the previous alert list. The alert list 818, in exemplary aspects, may be presented in association with a suggested problem list such as the suggested problem list 618 of FIG. 6B, and/or an order list such as the order list 718 of FIG. 7B depending on the amount of available screen real estate on the mobile device 200, and/or depending upon the nature of the identified and/or selected clinically-relevant concept(s).

Turning now to FIG. 9, a flow diagram is depicted of an exemplary method 900 of creating a voice-assisted shorthand clinical note on a device. The device includes at least a touch screen interface and a microphone that captures a conversation between two users such as between a clinician and a patient. At a step 910, the conversation is analyzed by, for example, a natural language processing component such as the natural language processing component 318 of FIG. 3 to identify one or more clinically-relevant concepts.

At a step 912, the identified concepts are presented in a first display area of the touch screen interface by a presenting component such as the presenting component 322 of FIG. 3. The concepts are selectable such that selection of a concept causes it to be populated into a clinical note display area of the touch screen interface. A user, such as the clinician, can use the device's keypad to input additional information concerning, for instance, a selected concept. The additional information is populated into the clinical note display area.

The concepts are presented in the first display area at substantially the same time as they are spoken in the conversation. Moreover, the concepts are presented in the order in which they occur in the conversation. In exemplary aspects, each concept is presented for a predetermined period of time such as one second, two seconds, three seconds, four seconds, or five seconds, or presented until replaced by newly identified clinically-relevant concepts.

Turning to FIG. 10, a flow diagram is depicted of an exemplary method 1000 of creating a voice-assisted shorthand clinical note on a mobile device where the mobile device includes a touch screen interface and a microphone used to capture a conversation between users such as a between a clinician and a patient. At a step 1010, a natural language processing component identifies clinically-relevant concepts in the conversation. The concepts may comprise, for example, symptoms, anatomical terms, conditions, tests, results, diagnoses, medications, procedures, orders, surgeries, dates, measurement units, numbers, and the like.

At a step 1012, the identified concepts are temporarily presented in a first display area of the mobile device substantially simultaneously as when they are spoken in the conversation. The first display area may be located adjacent to and above the device's keypad. Temporarily presenting the clinically-relevant concepts means that the concepts are presented for a predetermined period of time or until new clinically-relevant concepts are identified. If the concept is not selected, the concept is no longer presented.

At a step 1014, a selection of at least one of the concepts in the first display area is received by a receiving component such as the receiving component 316 of FIG. 3. At a step 1016, the selected concept is populated into a clinical note display area of the mobile device. Although clinically-relevant concepts are only temporarily presented in the first display area, it is contemplated that the selected concepts in the clinical note display area remain presented until either manually deleted by the user or the application is terminated.

The method 1000 may additionally comprise presenting a modifier list in conjunction with the clinical note display area. The modifier list may include one or more selectable modifiers. Upon a modifier being selected, it is populated into the clinical note display area where it can be used to modify or add context to one of the selected concepts. In an additional exemplary aspect, a list of possible or suggested problems may be automatically presented upon determining that the possible problems are relevant to one or more of the identified and/or selected concepts. Each of the suggested problems is selectable and selection of a problem adds it to the patient's problem list in the patient's EMR. Continuing, it is further contemplated that a list of order sets may be automatically presented upon determining that the order sets are relevant to one or more of the identified and/or selected concepts. Each of the order sets is selectable and selection of an order set may initiate the order set. Additionally, it is contemplated that one or more alerts may be automatically presented upon determining that the alert is relevant to one or more of the identified and/or selected concepts. The alerts are selectable and selection of an alert may cause the alert to be stored in the patient's EMR and flagged for attention by the user of the mobile device.

As seen, the present invention provides a quick and easy way for a clinician to create a voice-assisted shorthand clinical note on a mobile device that may be used as the basis for the later generation of a more comprehensive clinical note. By using natural language processing to identify particularly relevant terms in a conversation, and by presenting just these terms on the mobile device, the clinician can rapidly decide which terms are the most useful memory prompts. Further, the invention as described enables the clinician to closely attend to what the patient is saying which further enhances the clinician/patient relationship.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computerized method, carried out by at least one server having one or more processors, of utilizing natural language processing to generate a user interface for display on a touch screen of a mobile device associated with a clinician, wherein the user interface facilitates creation of a voice-assisted shorthand clinical note on the mobile device in real time, wherein the mobile device includes a microphone to capture a spoken conversation between a patient and a clinician, the method comprising:

capturing the spoken conversation between the patient and the clinician;

as the spoken conversation is in progress between the patient and the clinician, substantially simultaneously:
converting the spoken conversation into a text stream,
analyzing the text stream to determine a presence of one or more clinically-relevant concepts in the text stream by applying a set of rules to text in the text stream using a natural language processing system by matching at least a portion of the text in the text stream to the one or more clinically-relevant concepts, and
extracting the one or more clinically-relevant concepts from the text stream and temporarily presenting, via the user interface, the one or more clinically-relevant concepts in a first display area of the user interface, wherein the one or more clinically-relevant concepts are selectable;

receiving a selection, from the clinician, of at least one clinically-relevant concept from the one or more clinically-relevant concepts and populating the selected at least one clinically-relevant concept into a clinical note display area of the user interface, wherein the clinical note display area is adjacent to the first display area of the user interface;

substantially simultaneously determining that the at least one clinically-relevant concept selected by the clinician comprises an indication of a symptom, a set of symptoms, or a diagnosis;

upon determining that the at least one clinically-relevant concept selected by the clinician comprises the indication of the symptom, the set of symptoms, or the diagnosis, automatically determining, in real time, one or more of at least one suggested problem list, at least one orders set, and at least one alert corresponding to the at least one clinically-relevant concept by utilizing one or more of differential diagnoses lists, standards-of-care, and best practices stored in a data store;

temporarily presenting the one or more of the determined at least one suggested problem list, the at least one orders set, and the at least one alert on a second display area of the user for further selection by the clinician;

upon receiving further selection from the clinician of at least one of the one or more of the determined at least one suggested problem list, the at least one orders set, and the at least one alert, dynamically updating the clinical note display area by populating the clinical note display area of the user interface according to the further selection; and as the spoken conversation is in progress between the clinician and the patient, dynamically updating and adjusting display parameters of at least one of the first display area, the clinical note display area, and the second display area of the user interface for maximizing screen real estate of the touch screen of the mobile device.

2. The method of claim 1, wherein the at least one clinically-relevant concept is presented in the first display area of the touch screen of the mobile device for a predetermined period of time.

3. The method of claim 1, wherein the at least one clinically-relevant concept is spoken by the patient.

4. The method of claim 1, wherein the at least one clinically-relevant concept is spoken by the clinician.

5. The method of claim 1, further comprising:
receiving one or more text-based entries inputted into the mobile device using a keypad associated with the mobile device; and
populating the one or more text-based entries into the clinical note display area of the touch screen of the mobile device.

6. One or more non-transitory computer-readable media having computer-executable instructions embodied thereon that, when executed, generate a dynamic user interface for display on a touch screen of a mobile device associated with a clinician, wherein a spoken conversation between a patient and the clinician is captured using a microphone associated with the mobile device and substantially simultaneously is automatically converted into a text stream for analysis, wherein the dynamic user interface displayed on the touch screen of the mobile device comprises:
a first display area that temporarily presents one or more selectable clinically-relevant concepts identified from the text stream of the spoken conversation between the patient and the clinician by using a natural language processing system and matching at least a portion of text in the text stream to the one or more selectable clinically-relevant concepts, wherein the one or more selectable clinically-relevant concepts are presented on the first display area at substantially the same time as they are spoken by the patient or the clinician in the spoken conversation;
a clinical note display area presented at the same time as the first display area, wherein upon receipt of a selection of at least one of the one or more selectable clinically-relevant concepts presented in the first display area, becomes populated with the selected at least one of the one or more selectable clinically-relevant concepts in real time wherein, when a determination that the selected at least one of the one or more selectable clinically-relevant concepts comprises a symptom, a set of symptoms, or a diagnosis, automatically determining, in real time, one or more of at least one suggested diagnoses list, at least one orders set, and at least one alert corresponding to the selected at least one of the one or more selectable clinically-relevant concepts by utilizing one or more of differential diagnoses lists, standards-of-care, and best practices stored in a data store;
a diagnoses list display area for dynamically displaying the at least one suggested diagnoses list;
an order display area for dynamically displaying the at least one orders set; and
an alert display area for dynamically displaying the at least one alert, wherein as the spoken conversation between the patient and the clinician progresses, dynamically updating and adjusting display parameters of at least one of the first display area, the clinical note display area, the diagnoses list display area, the order display area, and the alert display area.

7. The media of claim 6, wherein the user interface further comprises a modifier display area for presenting a predefined set of selectable modifiers.

8. The media of claim 7, wherein the predefined set of selectable modifiers comprises one or more of the following: "confirmed," "ruled-out," "negative," "positive," "yes," "no," or "contraindicated".

9. The media of claim 8, wherein selection of at least one modifier of the predefined set of modifiers causes the selected modifier to be populated into the clinical note display area.

10. The media of claim 6, wherein the at least one orders set displayed in the order display area comprises one or more selectable orders corresponding to the at least one of the one or more clinically-relevant concepts selected by the clinician.

11. The media of claim 6, wherein the at least one suggested diagnoses list displayed in the diagnoses list display area comprises one or more selectable diagnoses corresponding to the at least one of the one or more clinically-relevant concepts selected by the clinician.

12. One or more non-transitory computer-readable media having computer-executable instructions embodied thereon that, when executed, facilitate a method of generating a user interface for display on a display screen of a mobile device, wherein the user interface is usable for creating a voice-assisted shorthand clinical note using natural language processing, in real time, and wherein the mobile device comprises a microphone for capturing a spoken conversation between a clinician and a patient, the method comprising:
capturing the spoken conversation between the patient and the clinician;
using natural language processing, identifying one or more clinically-relevant concepts in the spoken conversation;
extracting the one or more clinically-relevant concept from the spoken conversation;
temporarily presenting the one or more clinically-relevant concepts in a first display area of the user interface displayed on the display screen of the mobile device, wherein the one or more clinically-relevant concepts are presented at substantially the same time as the one or more clinically-relevant concepts are spoken in the spoken conversation between the clinician and the patient;
receiving a selection, from the clinician, of a first clinically-relevant concept of the one or more clinically-relevant concepts while the first clinically-relevant concept is being presented in the first display area;
presenting the first clinically-relevant concept in a clinical note display area of the user interface displayed concurrently with the first display area on the display screen of the mobile device;
determining if the first clinically-relevant concept selected by the clinician comprises a symptom, a set of symptoms, or a diagnosis;
upon determining that the first clinically-relevant concept selected by the clinician comprises a symptom, a set of symptoms, or a diagnosis, automatically determining, in real time, one or more of at least one suggested problem list, at least one orders set, and at least one alert corresponding to the first clinically-relevant concept; and
presenting the determined at least one suggested problem list in a suggested problem list display area of the user interface, the at least one orders set in an orders set display area of the user interface, and the at least one alert in an alert display area of the user interface, for selection by the clinician, wherein as the spoken conversation is in progress between the clinician and the patient, dynamically updating and adjusting display parameters of at least one of the first display area, the suggested problem list display area, the orders set display area, and the alert display area of the user interface, as the user interface becomes updated with the one or more clinically-relevant concepts identified from the spoken conversation in real time.

13. The media of claim 12, wherein the one or more clinically-relevant concepts comprise one or more of the following: medical conditions, diagnoses, procedures, anatomical terms, medical symptoms, numerical values, measurement units, results, tests, or dates.

14. The media of claim 12, wherein when a second clinically-relevant concept of the one or more clinically-relevant concepts is not selected within a predetermined period of time, removing the unselected second clinically-relevant concept from the first display area of the user interface displayed on the display screen of the mobile device.

15. The media of claim 12, wherein the one or more clinically-relevant concepts are presented in the first display area of the user interface displayed on the display screen of the mobile device, in an order in which they are spoken in the spoken conversation between the clinician and the patient.

16. The media of claim 12, further comprising:
receiving a selection of a second clinically-relevant concept of the one or more clinically-relevant concepts while the second clinically-relevant concept is being presented in the first display area of the user interface displayed on the display screen of the mobile device; and presenting the second clinically-relevant concept in the clinical note display area of the user interface.

17. The media of claim 16, wherein the first clinically-relevant concept and the second clinically-relevant concept are presented in the clinical note display area in an order in which they are selected.

18. The media of claim 12, wherein the first display area is positioned on the user interface such that it is displayed adjacent to a keypad displayed on the display screen of the mobile device.

* * * * *